(12) United States Patent
Okutani et al.

(10) Patent No.: US 10,405,823 B1
(45) Date of Patent: Sep. 10, 2019

(54) RADIATION IMAGING APPARATUS

(71) Applicant: SHIMADZU CORPORATION, Kyoto-shi (JP)

(72) Inventors: Keita Okutani, Kyoto (JP); Masahiro Tanaka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/123,366

(22) Filed: Sep. 6, 2018

(51) Int. Cl.
*A61B 6/00* (2006.01)
*H05G 1/56* (2006.01)
*A61B 6/10* (2006.01)
*A61B 6/06* (2006.01)

(52) U.S. Cl.
CPC ............... *A61B 6/548* (2013.01); *A61B 6/06* (2013.01); *A61B 6/107* (2013.01); *H05G 1/56* (2013.01)

(58) Field of Classification Search
CPC .. G01N 23/043; G01N 21/6486; A61B 6/548; A61B 6/06; A61B 6/107; H05G 1/56
See application file for complete search history.

(56) References Cited

U.S. PATENT DOCUMENTS

| 2004/0236547 | A1* | 11/2004 | Rappaport | G06F 17/509 703/2 |
| 2009/0224935 | A1* | 9/2009 | Kagermeier | A61B 6/467 340/13.24 |
| 2011/0288853 | A1* | 11/2011 | Butzine | A61B 6/4405 704/8 |
| 2014/0254758 | A1* | 9/2014 | Saigusa | A61B 6/545 378/62 |

FOREIGN PATENT DOCUMENTS

| JP | 63-272328 | 11/1988 |
| JP | 7-261010 | 10/1995 |
| JP | 2000-137107 | 5/2000 |
| JP | 2006-286412 | 10/2006 |
| JP | 2006-314791 | 11/2006 |
| JP | 2007-233817 | 9/2007 |
| JP | 2013-512065 | 4/2013 |

OTHER PUBLICATIONS

JP 2016-038520 Notification of Reasons for Refusal dated Mar. 19, 2019, 2 pages—English, 2 pages—Japanese.

* cited by examiner

*Primary Examiner* — Yara B Green
(74) *Attorney, Agent, or Firm* — Andrew F. Young, Esq.; Lackenbach Siegel, LLP

(57) ABSTRACT

A radiation imaging apparatus secures subject safety and includes a wireless communication unit of an operation panel and a wireless communication unit of a control unit performing periodical wireless communication. While operating, it is determined if wireless communication unit of the control unit is receiving a wireless communication signal from the wireless communication unit of the operation panel, or not. Then, when the wireless communication unit of the control unit is not receiving the wireless communication signal from the wireless communication unit of the operation panel, a movement control element of the control unit executes an emergency shutdown operation to halt movement of a support table, a X-ray tube, a collimator and a X-ray detector.

2 Claims, 6 Drawing Sheets

RADIATION IMAGING APPARATUS

CROSS REFERENCE TO RELATED APPLICATIONS

This application relates to, but does not claim priority from, JP 2016-038520 filed Mar. 1, 2016 and published as JP 2017-153641 on Sep. 7, 2017, the entire contents of which are incorporated herein by reference.

FIGURE SELECTED FOR PUBLICATION

FIG. 3.

BACKGROUND OF THE INVENTION

Field of the Invention

The present invention relates to a radiation imaging apparatus and particularly, relates to the radiation imaging apparatus operative via an operation panel that is wirelessly connected with the radiation imaging apparatus.

Description of the Related Art

A radiation imaging apparatus as an X-ray fluoroscopy base comprises a table on which a subject is laid, an X-ray tube and an X-ray detector that detects an X-ray irradiated from the X-ray tube and transmitting the subject, wherein the operator operates an operation unit to move the X-ray tube and the X-ray detector, and the table and so forth. In such a case, given the operation unit to carry out such an operation is an operation panel wirelessly connected with the main unit, a safety improvement, a space saving and a design (structure) improvement is achievable.

Patent Document 1 discloses the medical examination device or the therapy apparatus that shutdowns (suspends) the device operation thereof when a detection device detects that the operative element corresponding to the operation panel moves outside the room.

RELATED PRIOR ART DOCUMENTS

Patent Document 1—JP 2006-314791 A1

ASPECTS AND SUMMARY OF THE INVENTION

Relative to such an X-ray fluoroscopy imaging apparatus, an emergency shutdown button is equipped considering the safety for the subject and the reduction of the risk due to the unintentional operation of the device when the X-ray tube, the X-ray detector and the table and so forth are subject to movement. As set forth above, in the case in which the operation panel wirelessly connected with the main unit is adopted, such an emergency shutdown button is also equipped with the operation panel.

Such an emergency shutdown button must suspend immediately and securely the operation per se when operated (activated), so that in the case of adopting the main unit and the operation panel connected therewith, the safely must be secured assuredly even when an impairment relative to the wireless communication between the main unit and the operation panel takes place or a trouble relative to the operation of the operation panel is infected.

The present invention is completed to solve such above problems, and the purpose of the present invention is to provide the radiation imaging apparatus that assuredly secures the safety of the subject even when the impairment relative to the wireless communication between the radiation imaging apparatus and the operation panel takes place or a trouble relative to the operation of the operation panel occurs.

Means for Solving the Problem

According to an aspect of the invention in claims, a radiation imaging apparatus comprises: a radiation imaging unit comprising a movement member that moves for radiation imaging and a control unit that controls the movement of the movement member; and an operation panel that the control unit of the radiation imaging unit connects therewith; wherein the operation panel further comprises an operation member that moves the movement member and an emergency shutdown operation member that enforces an emergency shutdown (suspension) of the movement member, the operation panel and the control unit of the radiation imaging unit carries out a periodical wireless communicate in-between, and the control unit of the radiation imaging unit executes the emergency shutdown to halt the movement of the movement member when the periodical wireless communication is lost.

According to an aspect of another invention in claims, the control unit relative to the above radiation imaging unit further comprises an emergency operation cancel unit to cancel the emergency shutdown operation even when the periodical wireless communication is lost.

According to an aspect of the invention claimed in claims, the radiation imaging unit comprises: a table as the movement member, on which a subject is loaded, a radiation irradiation unit; and a radiation detector, wherein the control unit of the radiation imaging unit controls movements of the table, the radiation irradiation unit, and the radiation detector.

Effect of the Invention

According to the aspect of the invention claimed in claims, the emergency shutdown operation is executed to halt the movement of the movement member when the periodical wireless communication is lost, so that even when a trouble impairment relative to the wireless communication between the radiation imaging unit and the operation panel takes place or a trouble relative to the operation of the operation panel occurs, the safety for the subject is assuredly secured.

According to an aspect of another invention in claims, even when the periodical wireless communication is lost, the emergency operation cancel unit to cancel the emergency shutdown operation is equipped, so that even when the operation panel is inoperable, the radiation imaging is executable by operating the operation unit in the part of the radiation imaging unit.

According to an aspect of the invention claimed in claims, the movements of the table, the radiation irradiation unit and the radiation detector are halted in emergency shutdown and as a result, safety of the subject is secured without fail.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
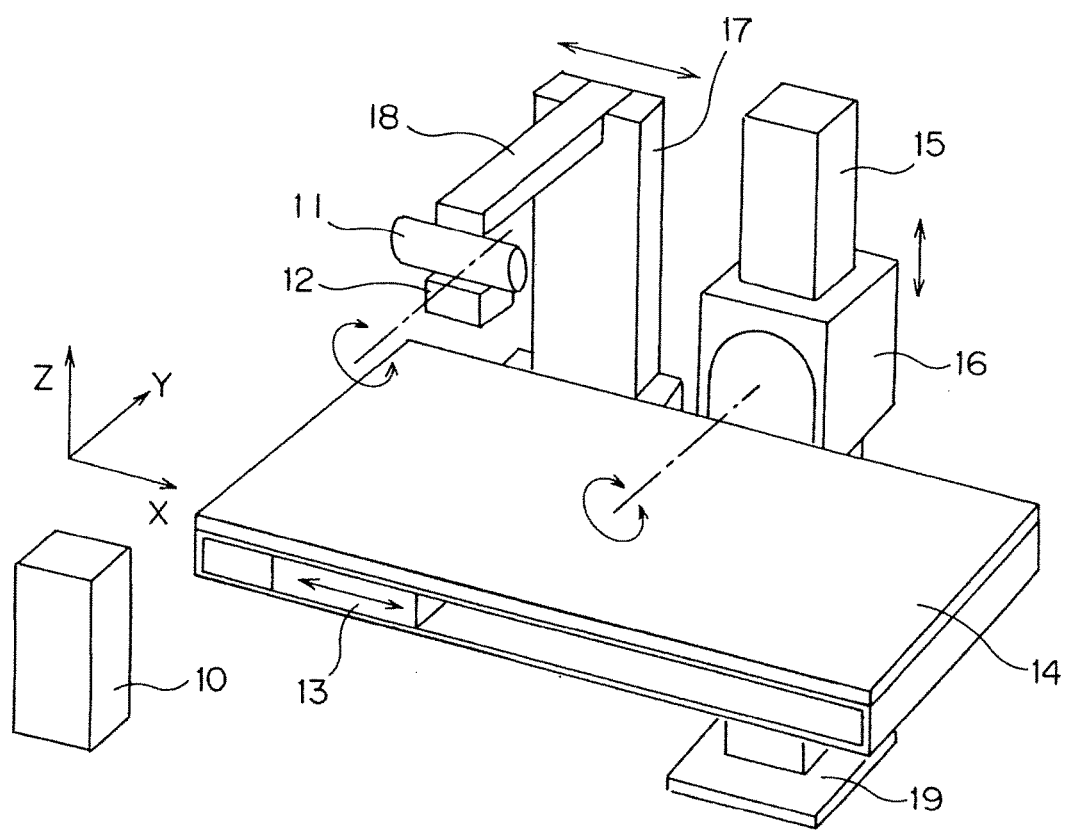
FIG. 1 is a perspective view illustrating an X-ray fluoroscopy imaging apparatus base according to the aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' or 'connect' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

The inventors set forth Embodiments of the present invention based on the following FIGs. FIG. 1 is a perspective view illustrating an X-ray fluoroscopy imaging apparatus as the X-ray imaging apparatus according to the aspect of the present invention.

The X-ray fluoroscopy imaging apparatus base comprises: a control unit 10 to control the entire device; a main supporting column 15 standing on the pedestal 19; a holding unit 16 that installed as operative in elevating relative to the main supporting column 15; a table 14 that is rotatable relative to the holding unit 16; an arm 18 that is operable in elevating relative to the supporting column 17 and hangs an X-ray tube 11 and a collimator 12; an X-ray detector 13, such as a flat panel detector, that is in-place underneath the surface of the table 14 and facing the X-ray tube 11; and an operation panel 20 as set forth later.

In addition, the X-ray tube 11 and the collimator 12 are operative as the radiation irradiation unit of the present invention. In addition, the X-ray detector 13 is operative as the radiation detector of the present invention. And, the aspects other than the operation panel 20 of the X-ray fluoroscopy imaging apparatus base is operative as the radiation imaging unit of the present invention.

In addition, the holding member 16 lifts and lowers in the Z-direction referring to FIG. 1. In addition, the table 14 rotates around the axis which is orthogonal to the longitudinal direction of the table 14 and facing the horizontal direction (axis in the direction facing Y-direction in FIG. 1). In addition, the support column 17 and the X-ray detector 13 shifts back-and-forth in synchronism with each other in the longitudinal direction of the table 14. In addition, the arm 18 along with the X-ray tube 11 and the collimator 12 lifts and lowers relative to the support column 17 in the Z-direction referring to FIG. 1. In addition, the X-ray tube 11 and the collimator 12 are oscillable around the arm 18 which is the center.

Figure 2:
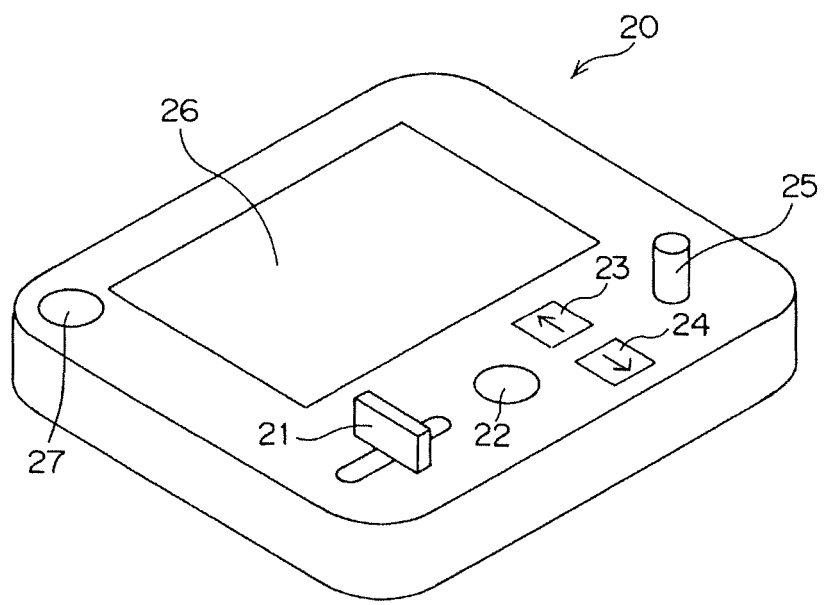
FIG. 2 is a perspective view illustrating the operation panel 20 of the present invention.

FIG. 2 is a perspective view illustrating the operation panel 20.

The operation panel 20 further comprises a rotation operation lever 21 that rotates the table 14 in synchronism with the X-ray tube 11, the collimator 12 and the X-ray detector 13, a mode switching button 22 that executes a variety of mode-switchings, an up-button 23 and a down-button 24 that ups and downs the table 14 in synchronism with the X-ray tube 11, the collimator 12 and the X-ray detector 13, and an imaging system operation lever 25 that moves an imaging system comprising the X-ray tube 11, the collimator 12 and the X-ray detector 13 in the longitudinal direction of the table 14. In addition, the operation panel 20 further comprises an input area 26 having a touchscreen feature. The other variety of information is input in the input area 26. In addition, the operation panel 20 further comprises an emergency shutdown button 27 as the emergency shutdown operation member that halts the movement of the table 14, the X-ray tube 11, the collimator 12 and the X-ray detector 13 and so forth in emergency shutdown. In addition, the operation panel 20 comprises such buttons that are operative to provide other functions, but not shown in FIG. 2.

When the X-ray fluoroscopy and the X-ray imaging are performed using the X-ray imaging apparatus comprising such structures, the control unit 10 incorporates the data and the anatomical program of the subject from the in-hospital network. Then, load the subject the table 14; up the table 14 together with the X-ray tube 11, the collimator 12 and the X-ray detector 13; and rotate table 14 together with the X-ray tube 11, the collimator 12 and the X-ray detector 13. In addition, move the X-ray tube 11, the collimator 12 and the X-ray detector 13 in the longitudinal direction of the table 14 and also, up and down the arm 18 relative to the table 14 with the X-ray tube 11 and the collimator 12. Accordingly, the relative locational relationship between the subject and the imaging system and the body tilting of the subject is adequate for the X-ray imaging and the X-ray fluoroscopy.

Figure 3:
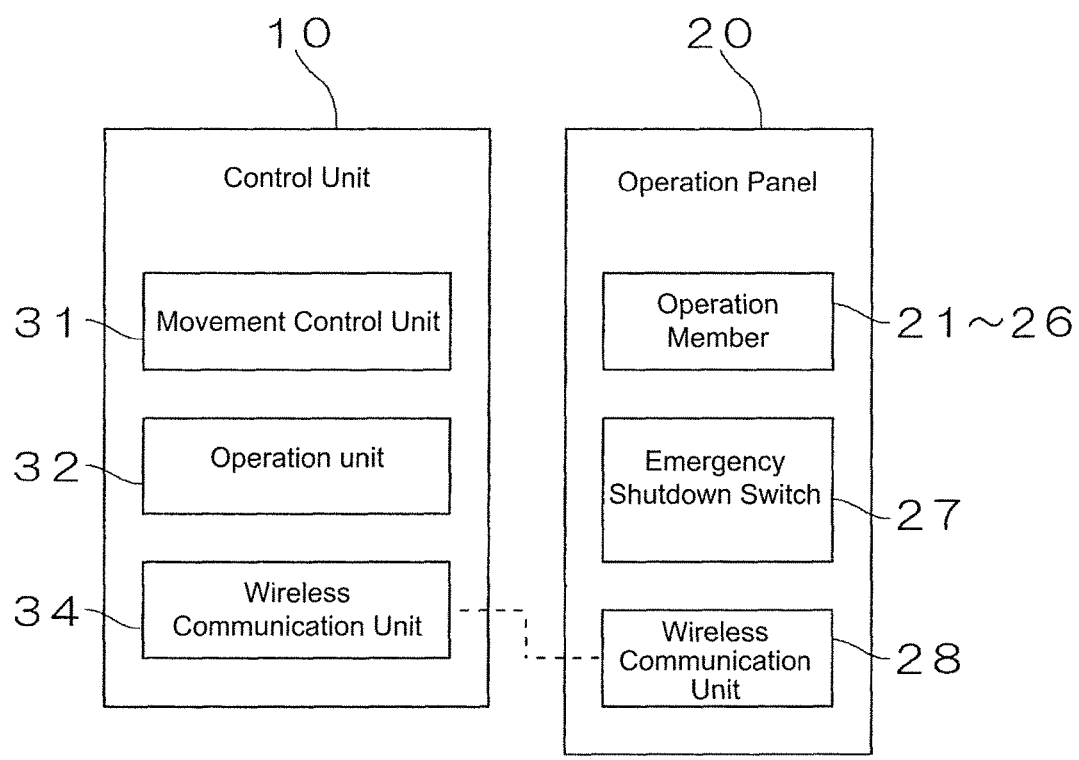
FIG. 3 is a block diagram illustrating the control unit 10 and the operation panel 20 of the X-ray fluoroscopy apparatus base according to an aspect of the Embodiment 1 of the present invention.

FIG. 3 is a block diagram illustrating the control unit 10 and the operation panel 20 of the X-ray fluoroscopy apparatus base according to an aspect of the Embodiment 1 of the present invention.

The control unit 10 comprises: a movement control element 31 that controls the movements of the table 14, the X-ray tube 11, the collimator 12 and the X-ray detector 13; an operation unit 32 having a keyboard and a touchscreen and so forth used to execute a variety of operations; and a wireless communication unit 34. The operation panel 20 further comprises: the operation members including such as the rotation operation lever 21, the mode switching button 22, the up-button 23, the down-button 24, the imaging system operation lever 25 and the input area 26 as set forth above; and the emergency shutdown button 27 as set forth above; and the wireless communication unit 28. The wireless communication unit 28 and the wireless communication unit 34 of the control unit 10 perform the periodical wireless communication.

Figure 4:
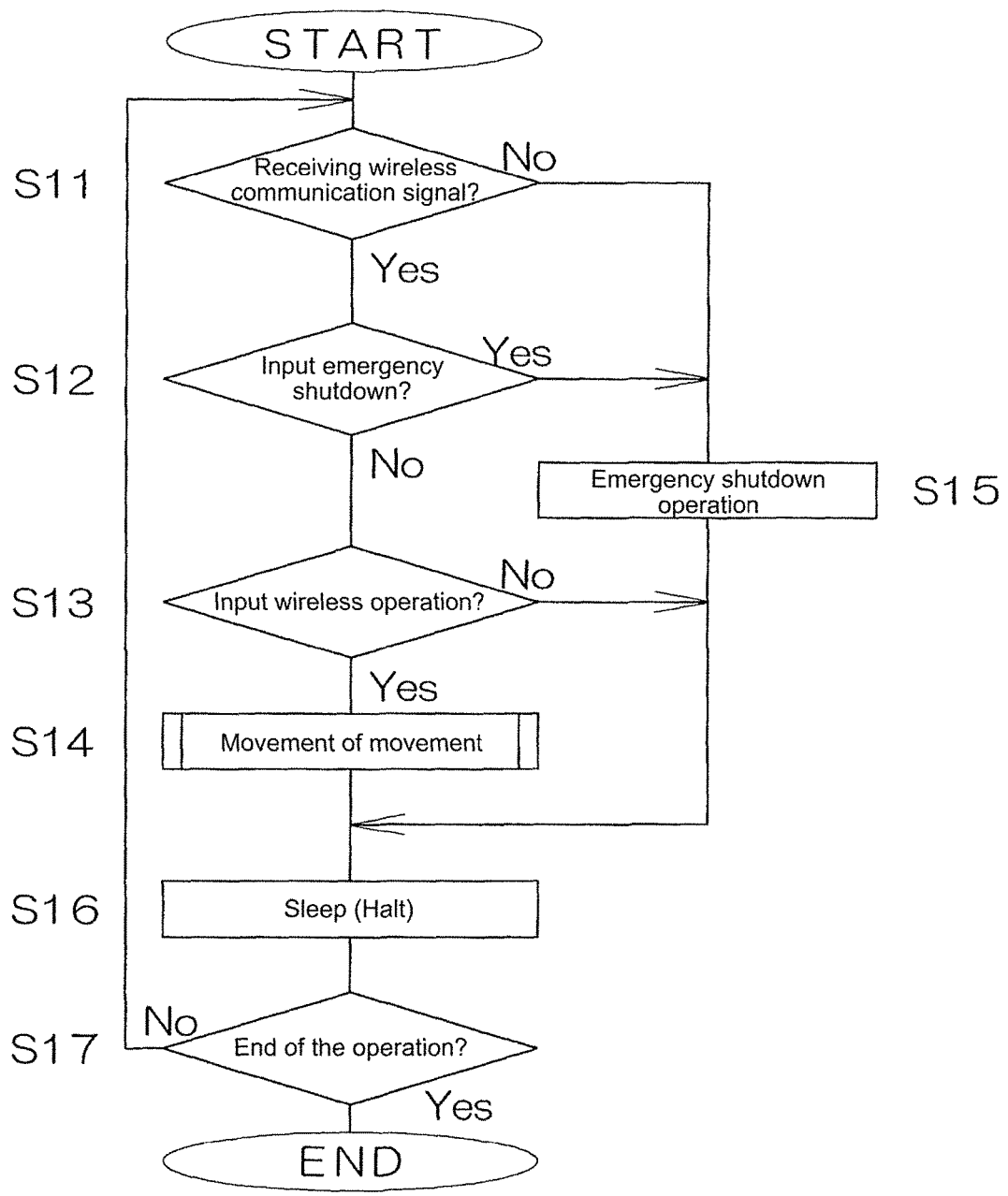
FIG. 4 is a flow-chart illustrating an operation when carrying out an X-ray fluoroscopy or an X-ray imaging relative to the X-ray fluoroscopic imaging apparatus base according to the aspect of the Embodiment 1 of the present invention.

Next, the inventors set forth the operation of the X-ray fluoroscopy imaging apparatus base as set forth above. FIG. 4 is a flow-chart illustrating an operation when carrying out the X-ray fluoroscopy or the X-ray imaging relative to the X-ray fluoroscopic imaging apparatus base according to the aspect of the Embodiment 1 of the present invention.

With regard to the X-ray fluoroscopic imaging apparatus base, as set forth above, the wireless communication unit 28 of the operation panel 20 and the wireless communication unit 34 of the control unit 10 perform the periodical wireless communication. When carrying out the X-ray fluoroscopy or the X-ray imaging, it is determined whether the wireless communication unit 34 of the control unit 10 is receiving a wireless communication signal from the wireless communication unit 28 of the operation panel 20 or not (step S11). Then, when the wireless communication unit 34 of the control unit 10 is not receiving the wireless communication signal from the wireless communication unit 28 of the operation panel 20, the movement control element 31 of the control unit 10 executes an emergency shutdown operation to halt urgently the movement of the table 14, the X-ray tube 11, the collimator 12 and the X-ray detector 13 (step S15).

As set forth above, the operation panel 20 comprises the operation shutdown button 27 to halt urgently the movement of the X-ray tube 11, the collimator 12 and the X-ray detector 13 and so forth. Accordingly, when a risk occurs about the subject, the movements of the table 14, the X-ray tube 11, the collimator 12 and the X-ray detector 13 and so forth are urgently shutdown to secure the safety for the subject. However, when any trouble takes place in the wireless communication between the control unit 10 and the operation panel 20 and any trouble takes place in the operation of the operation panel 20, the emergency shutdown operation is not operable using the emergency shutdown button 27. Therefore, with regard to the X-ray fluoroscopic imaging apparatus base, when the wireless communication unit 34 of the control unit 10 is unable to confirm receiving the wireless communication signal from the wireless communication unit 28 of the operation panel 20, the safety for the subject is secured assuredly by the emergency shutdown as set forth above.

When the wireless communication unit 34 of the control unit 10 is receiving the wireless communication signal from the wireless communication unit 28 of the operation panel 20, it is determined whether an input for the emergency shutdown is given by the operation of the emergency shutdown switch 27 of the operation panel 20 or not (step S12). When the input of the emergency shutdown is carried out, the movement control element 31 of the control unit 10 executes the emergency shutdown operation to halt urgently the movement of the table 14, the X-ray tube 11, the collimator 12 and the X-ray detector 13 (step S15).

When the input of the emergency shutdown is not carried out, it is determined whether the wireless input is carried out by the operation of the operation members including such as the rotation operation lever 21, the mode switching button 22, the up-button 23, the down-button 24, the imaging system operation lever 25 and the input area 26 and so forth of the operation panel 20 or not (step S13). Then, when the wireless input is carried out, the movement member including the table 14, the X-ray tube 11, the collimator 12 and the X-ray detector 13 and so forth are moved (step S14).

Then, following a sleep (suspending) for a predetermined time period (step S16), either the X-ray fluoroscopy or the X-ray imaging is carried out and then the operation ends followed by turning off the power (step S17), and then such operation are repeated.

Figure 5:
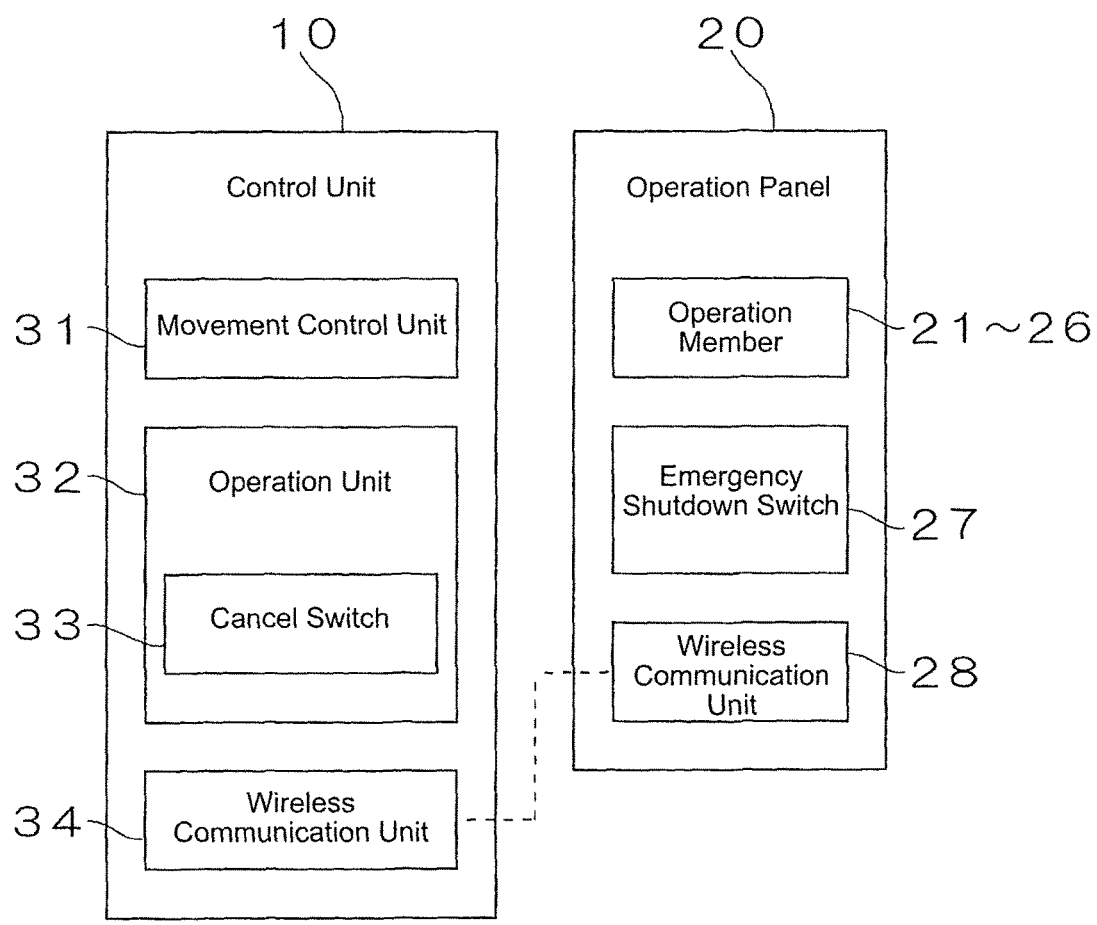
FIG. 5 is a block diagram illustrating the control unit 10 and the operation panel 20 of the X-ray fluoroscopy apparatus base according to an aspect of the Embodiment 2 of the present invention.

Next, the inventors set forth the other Embodiments of the present invention. FIG. 5 is a block diagram illustrating the control unit 10 and the operation panel 20 of the X-ray fluoroscopy apparatus base according to an aspect of the Embodiment 2 of the present invention. Further, the same member as illustrated according to the aspect of the Embodiment 1 set forth above is not set forth while providing the identical reference sign.

The X-ray fluoroscopic imaging apparatus base, according to the aspect of the Embodiment 2, further comprises a cancel switch 33 in the operation unit 32 of the control unit 10 as the emergency operation cancel operation that cancels the emergency shutdown operation, as set forth above, even when the periodical wireless communication between the wireless communication unit 28 of the operation panel 20 and the wireless communication unit 34 of the control unit 10 is lost.

Figure 6:
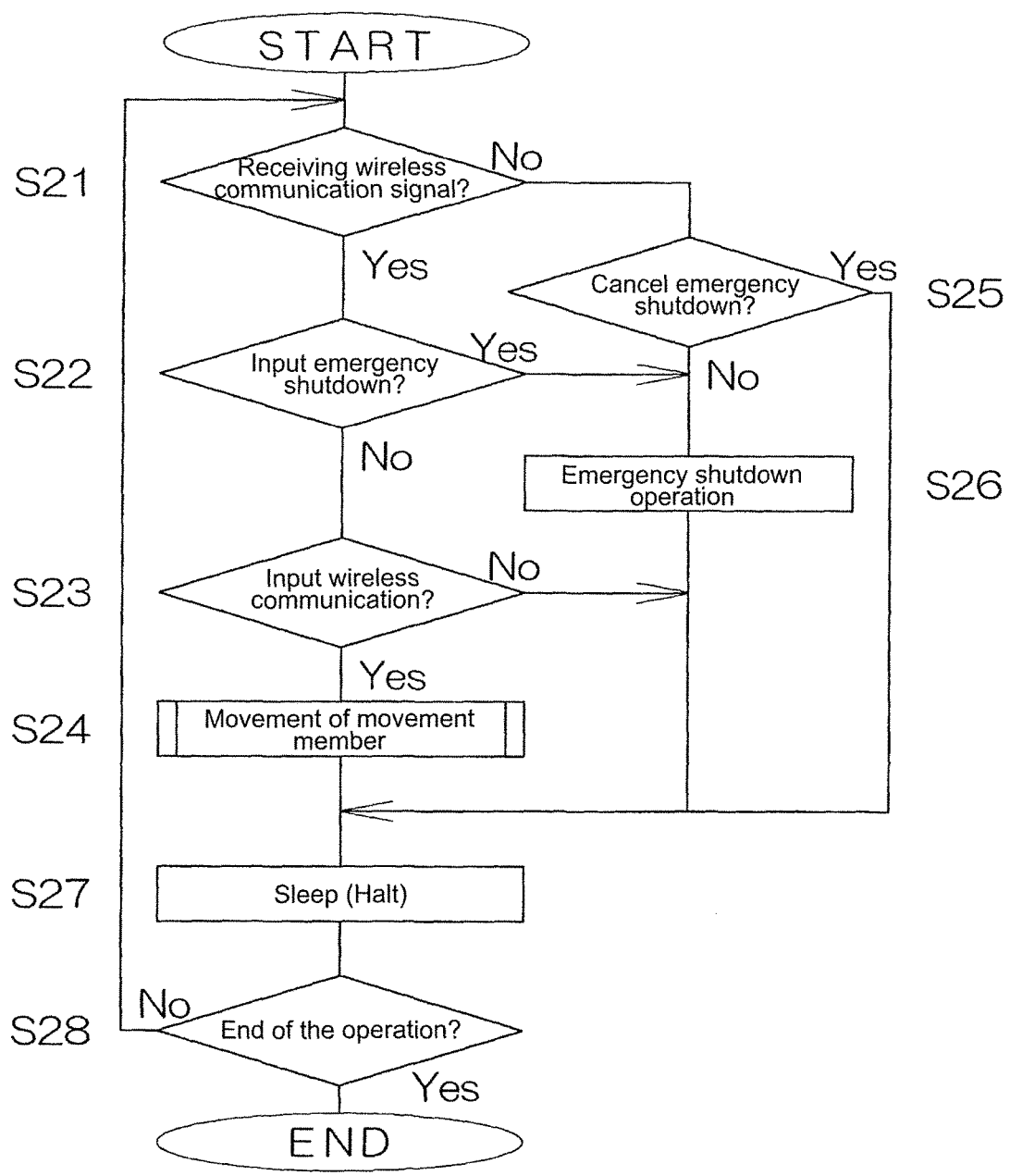
FIG. 6 is a flow-chart illustrating an operation when carrying out an X-ray fluoroscopy or an X-ray imaging relative to the X-ray fluoroscopic imaging apparatus base according to the aspect of the Embodiment 2 of the present invention.

FIG. 6 is a flow-chart illustrating an operation when carrying out the X-ray fluoroscopy or the X-ray imaging relative to the X-ray fluoroscopic imaging apparatus base according to the aspect of the Embodiment 2 of the present invention. In addition, the detail explanation of the same step referring to FIG. 4 is not set forth here.

With regard to the X-ray fluoroscopic imaging apparatus base according to the aspect of the Embodiment 2, as well as the Embodiment 1 set forth above, when the wireless communication unit 28 of the operation panel 20 and the wireless communication unit 34 of the control unit 10 are communicating and the X-ray fluoroscopy or the X-ray imaging is being carried out, it is determined whether the wireless communication unit 34 of the control unit 10 is receiving the wireless communication signal from the wireless communication unit 28 of the operation panel 20 or not (step S21). Then, when the wireless communication unit 34 of the control unit 10 is not receiving the wireless communication signal from the wireless communication unit 28 of the operation panel 20, the control unit 10 determines whether the cancel switch 33 of the operation unit 32 is operative and the emergency shutdown operation is under the canceled state or not (step S25).

When the cancel switch 33 is off and the emergency shutdown operation is not canceled, as well as the Embodiment 1, the movement control element 31 of the control unit 10 executes the emergency shutdown operation to halt urgently the movements of the table 14, the X-ray tube 11, the collimator 12 and the X-ray detector 13 (step S26).

On the other hand, in the case of that the cancel switch 33 is on and the emergency shutdown operation is canceled, even when the wireless communication unit 34 of the control unit 10 is not receiving the wireless communication signal from the wireless communication unit 28 of the operation panel 20, the movement control element 31 of the control unit 10 does not execute an emergency shutdown operation. In such a case, the X-ray fluoroscopy or the X-ray imaging using the operation unit 32 of the control unit 10 is performed.

In such a way, with regard to the X-ray fluoroscopic imaging apparatus base according to the aspect of the Embodiment 2, when the operation panel 20 is unavailable, the X-ray fluoroscopy or the X-ray imaging is executable by operating the operation unit 32 of the control unit 10.

REFERENCE OF SIGNS

10 Control unit
11 X-ray tube
12 Collimator
13 X-ray detector
14 Table
15 Main supporting column
16 Holding member
17 Supporting post
18 Arm
19 Pedestal
20 Operation panel
27 Emergency shutdown button
28 Wireless communication unit
31 Movement control unit
32 Operation unit
33 Cancel switch
34 Wireless communication unit As used herein, a computer system broadly includes some form of an input device for receiving data, an output device for outputting data in tangible form (e.g. printing or transmitting data, or displaying on a computer screen), a memory for storing data as well as computer code, and a processor/microprocessor for executing computer code wherein said computer code resident in the memory will physically cause said processor/microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related radiotherapy imaging devices, systems, and arrangements, including related radiotherapy tracking computers and operational controls and technologies of radiographic devices and all their sub components, including various circuits and components and combinations of circuits and combinations of components for such devices and for all related hand held type devices, without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, operating circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuit illustrations, step-modes, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

Those of skill in the particular art will be recognized as having and having access to sophisticated radiotherapy tracking systems, circuits, and methods such that the skill level is high in science, technology, computers, programming, circuit design, and arrangement such that the described elements herein, after and following a review of this inventive disclosure and the inventive details herein, will be understood by those of skill in the art.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical of any kind developed now or later developed e.g. the computer hard drive, a removable disk or media such as a memory stick or SD media, or other electronic recording medium. The programs may also be run locally, on a station, or over an open or closed network without limitations thereto, for example, with a server or other machine sending signals to the local machine, which allows the local machine to carry out the operations described herein.

Also, the inventors intend that only those claims which use the words "means for" (specifically requiring the phrase "for" in "means for") are intended to be interpreted under 35 USC 112 (f) paragraph. Moreover, no limitations from the specification are intended to be read into any claims, unless those limitations are expressly included in the claims.

It will be further understood that the method steps described herein shall be understood additionally as descriptive algorithms for the operation of the enclosed units, switches, modes, and devices and units to which they apply.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation imaging apparatus, comprising:
a radiation imaging unit, further comprising:
    a movement member that moves for executing a radiation imaging;
    a control unit that controls a movement of said movement member; and
    an operation panel that wirelessly connects with said control unit of said radiation imaging unit;
wherein, said operation panel further comprises:
    an operation member that moves said movement member and an emergency shutdown operation member that enforces an emergency shutdown of said movement of said movement member;
    operation and said control unit of said radiation imaging unit operable to carry out a periodical wireless communication in-between, and said control unit of said radiation imaging unit executes said emergency shutdown to halt said movement of said movement member when said periodical wireless communication is lost; and
wherein:
    said control unit of said radiation imaging unit further comprises:
    an emergency operation cancel unit that cancels said emergency shutdown operation even when said periodical wireless communication is lost regardless of a specific control function of said periodical wireless communication.

2. The radiation imaging apparatus, according to claim 1, wherein:

said radiation imaging unit, further comprises:
  said movement member that includes a table on which a subject is laid, a radiation irradiation unit and a radiation detector, and
said control unit of said radiation imaging unit controls movements of said table, said radiation irradiation unit, and said detector.

\* \* \* \* \*